United States Patent [19]

Sugasawa

[11] 4,410,730
[45] Oct. 18, 1983

[54] PROCESS FOR THE PRODUCTION OF O-(N-MONOSUBSTITUTED AMINO)BENZYL ALCOHOLS

[75] Inventor: Tsutomu Sugasawa, Kobe, Japan

[73] Assignee: Shionogi & Co., Ltd., Osaka, Japan

[21] Appl. No.: 53,183

[22] Filed: Jun. 28, 1979

Related U.S. Application Data

[63] Continuation of Ser. No. 675,892, Apr. 12, 1976, abandoned.

[51] Int. Cl.$^3$ .............................................. C07C 87/28
[52] U.S. Cl. ........................................ 564/327; 564/9
[58] Field of Search ............................................ 260/570

[56] References Cited

PUBLICATIONS

Olah, "Friedel–Crafts and Related Reactions", vol. I, p. 413 and vol. II, pp. 597–599, (1964).
Mueller et al., "Chemical Abstracts", vol. 56, pp. 12713–12715, (1962).

Primary Examiner—Robert V. Hines
Attorney, Agent, or Firm—Wenderoth, Lind & Ponack

[57] ABSTRACT

Process for the production of o-(N-monosubstituted amino)benzyl alcohols which comprises reacting an N-mono-substituted aniline optionally having one or more substituents with a boron trihalogenide at a temperature from about 0° C. to about 100° C. and reacting the resultant boron compound with an aldehyde in the presence of a base at a temperature from about −30° C. to about 100° C. to regiospecifically introduce a 1-hydroxy-alkyl or 1-hydroxy-substituted alkyl group into the ortho position of said aniline.

8 Claims, No Drawings

PROCESS FOR THE PRODUCTION OF O-(N-MONOSUBSTITUTED AMINO)BENZYL ALCOHOLS

This is a continuation of application Ser. No. 675,892, filed Apr. 12, 1976 now abandoned.

The present invention relates to a chemical process for the production of o-(N-monosubstituted amino)benzyl alcohols by regiospecifically introducing a 1-hydroxyalkyl or 1-hydroxy-substituted alkyl group into the ortho position of N-monosubstituted anilines.

There has heretofore been known o-hydroxyalkylation of anilines which involves acylating a p-substituted aniline at the ortho position by the Freidel-Crafts reaction and then reducing the resultant o-acyl-p-substituted aniline to give p-substituted-o-aminobenzyl alcohol. The process, however, requires harsh conditions such as heating at a temperature of above 200° C. for 2-3 hours and affords an unsatisfactory yield. Thus, there has been substantially known no process for the production of o-aminobenzyl alcohols with high economy and a wide scope of application.

Giving consideration to the fact that a variety of useful starting compounds in the chemical industry and many synthetic intermediates of valuable medicinals are o-(N-monosubstituted amino)benzyl alcohols, the present inventor has eagerly investigated developing of a novel process for the production of the o-(N-monosubstituted amino)benzyl alcohols with high economy and a wide scope of application. Thus, the process of the present invention has been established.

The present invention involves a process for the production of o-(N-monosubstituted amino)benzyl alcohols which comprises reacting an N-monosubstituted aniline, optionally having one or more substituents, with a boron trihalogenide at a temperature from about 0° C. to about 100° C. and reacting the resultant boron compound with an aldehyde in the presence of a base at temperature from about −30° C. to about 100° C. to introduce regiospecifically a 1-hydroxyalkyl or 1-hydroxy-substituted alkyl group into the ortho position of said aniline. Extreme broadness in the scope of application is one of the characteristics of the process of this invention, and the reaction model in which methylaniline is used as a starting compound is illustrated for ready understanding in the following scheme:

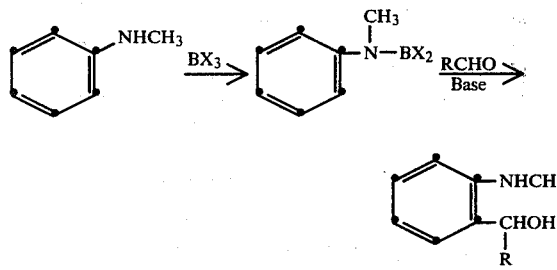

[wherein R represents a hydrogen, alkyl, alkenyl, aralkyl, aralkenyl, or aryl group, and X represents a halogen. The hydrocarbon groups represented by R are optionally substituted by one or more substituents selected from halogens, alkyl, alkoxy, acyloxy, alkoxycarbonyl, trifluoromethyl, nitro and cyano groups.]

Alternatively the present invention involves a process for the production of the same products which comprises reacting an N-monosubstituted aniline, optionally having one or more substituents, with a boron trihalogenide in the presence of an aldehyde and base at a temperature of below 100° C. to regiospecifically introduce a 1-hydroxyalkyl or 1-hydroxy-substituted alkyl group into the ortho position of said aniline.

The starting material is an N-monosubstituted aniline optionally having one or more substituents, in which the N-substituent may involve an alkyl, alkenyl, alkynyl, aralkyl, or aryl group, optionally substituted by one or more further substituents selected from halogens, alkyl, cycloalkyl, alkoxy, nitro, cyano, and alkylsulfonyl groups. The benzene ring of said aniline may be substituted by a halogen, alkyl, aralkyl, aryl, alkoxy, aryloxy, aralkoxy, nitro, cyano, alkoxycarbonyl, or acyloxy group. The definition of said substituents may be complemented by the following illustration. The alkyl group involves methyl, ethyl, propyl, butyl, and amyl. The alkenyl group involves allyl, butenyl, pentenyl, and hexenyl. The alkynyl group involves propynyl, butynyl, pentynyl, and hexynyl. The aralkyl group involves benzyl, phenethyl, and phenylpropyl. The aralkenyl group involves cinnamyl and phenylbutenyl. The aryl group involves phenyl, tolyl, xylyl, naphthyl, pyridyl, thienyl, and furyl. The alkoxy group involves methoxy, ethoxy, propoxy, and butoxy. The aryloxy group involves phenoxy, naphthoxy, and pyridyloxy. The aralkoxy group involves benzyloxy, phenethyloxy, and phenylpropyloxy. The alkoxycarbonyl group involves methoxycarbonyl, ethoxycarbonyl, propoxycarbonyl, and butoxycarbonyl. The acyloxy group involves acetoxy, propionyloxy, butyryloxy, and pentanoyloxy. The cycloalkyl group involves cyclopropyl, cyclobutyl, cyclopentyl, and cyclohexyl. The alkylsulfonyl group involves methylsulfonyl, ethylsulfonyl, propylsulfonyl, and butylsulfonyl. The halogen involves chlorine, fluorine, and bromine.

The boron trihalogenide involves, illustratively, boron trichloride and boron tribromide.

As above described, another starting material is an aldehyde, being representable by the formula:

RCHO wherein R represents a hydrogen, alkyl (e.g. methyl, ethyl, propyl, butyl, pentyl, hexyl, amyl, stearlyl), alkenyl (e.g. vinyl, propenyl, butenyl, pentenyl), cycloalkyl (e.g. cyclopropyl, cyclobutyl, cyclopentyl, cyclohexyl), aralkyl (e.g. benzyl, phenethyl, phenylpropyl, phenylpentyl), aralkenyl (e.g. phenylvinyl, phenylpropenyl, phenylbutenyl), or aryl group (e.g. phenyl, tolyl, xylyl, naphthyl, pyridyl, thienyl, furyl). The aldehyde involves, illustratively, a saturated aliphatic aldehyde (e.g. formaldehyde, acetaldehyde, chloral, propionaldehyde, butyraldehyde, isobutyraldehyde, valeraldehyde, caproaldehyde, heptaldehyde, stearaldehyde), unsaturated aliphatic aldehyde (e.g. acrolein, crotonaldehyde, butenylaldehyde, pentenylaldehyde), cycloalkyl type aldehyde (e.g. cyclopropanecarboxaldehyde, cyclobutanecarboxaldehyde, cyclohexanecarboxaldehyde), aralkyl type aldehyde (e.g. phenylacetaldehyde, phenylbutyraldehyde, tolylhexaldehyde), aralkenyl type aldehyde (e.g. cinnamaldehyde, phenylpropenylaldehyde, tolylpentenylaldehyde), and aromatic aldehyde (e.g. benzaldehyde anisaldehyde, tolaldehydes, salcylaldehyde acetate, p-thymolaldehyde acetate, homosalicylaldehyde acetate, vanillin acetate, veratraldehyde, piperonal, furfural, 2-formylpyridine, naphthaldehydes). These aldehydes are optionally substituted with one or more inert substituents selected from halogens (e.g. chlorine, bromine, iodine, fluorine), alkyl (e.g. methyl, ethyl, propyl, isopropyl, butyl, isobutyl, pentyl), alkoxy (e.g. methoxy, ethoxy, propoxy, butoxy), acyloxy (e.g. acetoxy), alkoxycarbonyl (e.g. methoxycarbonyl, ethoxycarbonyl, propoxycarbonyl, butoxycarbonyl), trifluoromethyl, nitro, and cyano groups and may be used in a form of polymer such as paraldehyde.

The base used as a kind of catalyst in the second step of the present invention, involves illustratively, an organic amine, preferably secondary amine such as hindered dialkylamine (e.g. t-butylisopropylamine, diisopropylamine, di-t-butylamine), secondary cycloalkylamine (e.g. dicyclohexylamine, t-butylcyclohexylamine, isopropylcyclohexylamine), or secondary aromatic amine (e.g. t-butylaniline, isopropylaniline, cyclohexylaniline, diphenylamine), and tertiary amine such as tertiary alkylamine (e.g. triethylamine, tripropylamine, triisopropylamine, tributylamine, triisobutylamine, dibutylethylamine, dipropylisopropylamine, diisopropylethylamine, diisobutylamine, butylethylpropylamine, dipropylbutylamine), tertiary alicyclic amine (e.g. methylpyrrolidine, ethyldicyclohexylamine, butyldicyclohexylamine, ethylpiperidine, propylmorpholine), and tertiary aromatic amine (e.g. dimethylaniline, diethylaniline, methylethylaniline, dimethylbenzylamine, diethylbenzylamine, methylethylbenzylamine, picoline, 2,6-luthidine, 2,4,6-collidine, pyridine, 2-isopropylpyridine, 2-t-butylpyridine).

The process of the present invention consists of (1) a step of reacting an N-monosubstituted aniline, optionally having one or more substituents, with a boron trihalogenide at a temperature from about 0° C. to about 100° C. to give a boron compound and (2) a step of reacting the resultant boron compound with an aldehyde in the presence of a base at a temperature from about −30° C. to about 100° C. to give the objective o-(N-mono-substituted amino)benzyl alcohol. The present process can be practically effected with or without isolation of the intermediate boron compound (i.e. N-monosubstituted anilinoborane dihalogenide).

The first step can be effected by treating the N-monosubstituted aniline with a boron trihalogenide in a suitable inert solvent such as methylene chloride, dichloroethane, benzene, toluene, or xylene, if necessary, in the presence of an organic amine such as triethylamine, tributylamine, or dimethylaniline at a temperature from about 0° C. to about 100° C., preferably from about room temperature to about 100° C. A suitable amount of the boron trihalogenide for the N-monosubstituted aniline is about 1.0 to about 1.5 mol equivalent, preferably about 1.0 to about 1.2 mol equivalent.

The second step can be effected by treating the above-obtained boron compound with an aldehyde in the presence of a base in an inert solvent such as methylene chloride, dichloroethane, benzene, toluene, or xylene. The reaction may be carried out at a temperature from about −30° C. to about 100° C., preferably about 0° C. to about room temperature. A suitable amount of the aldehyde for the N-monosubstituted aniline is about 1.0 to about 1.5 mol equivalent, preferably about 1.0 to about 1.2 mol equivalent, and a suitable amount of the base for the N-monosubstituted aniline is at least about 1.0 mol equivalent, preferably about 1.0 to about 3.0 mol equivalent. The process of the present invention proceeds very smoothly and selectively through both steps, whereby the o-(N-monosubstituted amino)benzyl alcohols can be obtained in a good yield.

Alternatively the process of the present invention can be effected in a single step by treating the starting N-monosubstituted aniline, optionally having one or more substituents with a boron trihalogenide in the presence of an aldehyde and base at a temperature from about −30° C. to about 100° C., preferably about 0° C. to about room temperature. In this case the reaction proceeds smoothly as above.

Thus obtained o-(N-monosubstituted amino)benzyl alcohols are useful as starting materials in the chemical industry or as synthetic intermediates in the production of medicinals.

Presently preferred and practical embodiments of the present invention are illustratively shown in the following examples.

EXAMPLE 1

To a solution of boron trichloride (110 mg) in methylene chloride (5 ml), a solution of methylaniline (100 mg) in methylene chloride (1 ml) is added with ice cooling, and the resultant mixture is stirred with ice cooling for 1 hour. A solution of triethylamine (95 mg) in methylene chloride (1 ml) is added thereto with ice cooling, and the mixture is refluxed for 2 hours. Then, a solution of benzaldehyde (100 mg) and tri-n-butylamine (208 mg) in methylene chloride (2 ml) is added with ice cooling to the mixture, which is stirred at room temperature for 2 hours. The reaction mixture is mixed with ice pieces and shaken with methylene chloride. The methylene chloride layer is washed with aqueous sodium carbonate and a saturated brine in that order, and evaporated under reduced pressure to remove the solvent. The residue is chromatographed on a column of silica gel, and the product is recrystallized from chloroform-petroleum ether to give 2-methylaminobenzydrol (148 mg) as crystals melting at 124° to 126° C. The yield is 74.4%. [E. Testa, et al., Chemical Abstracts, 60, 6848b (1964)].

Ir $\nu_{max}^{CHCl_3}$ cm$^{-1}$: 3590 (OH), 3432 (NH).

NMR (CDCl$_3$) ϵ: 2.73 (3H, s., N-CH$_3$), 3.52 (2H, broad m., NH+OH), 5.78 (1H, s., =C$\underline{H}$—OH).

EXAMPLE 2

To a solution of boron trichloride (100 mg) in dry benzene (5 ml), a solution of p-chloromethylaniline (100 mg) in dry benzene (2 ml) is added with cold water cooling (7°–10° C.), and the resultant mixture is refluxed for 2 hours. Then, a solution of o-chlorobenzaldehyde (99 mg) and tri-n-butylamine (131 mg) in dry benzene (2 ml) is added thereto with cold water cooling, and the mixture is stirred at room temperature for 1 hour. The reaction mixture is mixed with ice pieces and shaken with ether. The ethereal layer is washed with aqueous sodium carbonate and a saturated brine in that order, dried over potassium carbonate, and evaporated under reduced pressure. The residue is chromatographed on a column of silica gel, and the product is recrystallized from chloroform-petroleum ether to give 2-methylamino-5,2'-dichlorobenzhydrol (174 mg) as crystals melting at 106° to 108° C. The yield is 87.4%.

Anal. Calcd. for C$_{14}$H$_{13}$ONCl$_2$: C, 59.58; H, 4.65; N, 4.97; Cl, 25.13. Found: C, 59.50; H, 4.47; N, 5.20; Cl, 24.83.

IR, $\nu_{max}^{CHCl_3}$, cm$^{-1}$: 3586 (OH), 3427 (NH).

NMR (CDCl$_3$) δ: 2.84 (3H, s., N—CH$_3$), 3.30 (2H, broad s., NH+OH), 6.12 (1H, s., =C$\underline{H}$—OH).

EXAMPLES 3-5

Using the starting compounds (I) and (II), each reaction is carried out as in Example 2, whereby the corresponding products (III) are obtained.

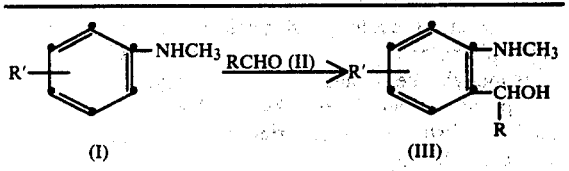

| Example No. | I R' | II R | Yield (%) | m.p. (°C.) | IR (CHCl₃, cm⁻¹) |
|---|---|---|---|---|---|
| 3 | H | o-NO₂—Ph | 96.8 | 93-95 | 3586, 3436 |
| 4 | H | p-NO₂—Ph | 79.3 | 127-128 | 3604, 3434 |
| 5 | p-Cl | Ph | 84.0 | 88.5-89 | 3430 (film) |

Note:
H (Hydrogen),
Ph (Phenyl group).

EXAMPLE 6

Using p-chloromethylaniline (100 mg) and benzaldehyde (90 mg) as starting materials, the reaction is effected as in Example 2, except that boron tribromide (195 mg) is used in lieu of boron trichloride, whereby 2-methylamino-5-chlorobenzhydrol (118 mg) is obtained as crystals melting at 88.5 to 89° C. The yield is 67.5%.

EXAMPLE 7

To a solution of boron trichloride (14.77 g) in toluene (60 ml), a solution of methylaniline (13.5 g) in toluene (30 ml) is added dropwise at −20° C. with stirring. A solution of triethylamine (12.8 g) in toluene (20 ml) is added to the above mixture, which is stirred at room temperature overnight. The precipitate is filtered under nitrogen atmosphere and washed with toluene. The filtrate and washings are combined, evaporated under reduced pressure to remove the toluene, and the residue is distilled to give N-methylanilinoborane dichloride (10.5 g) as an oil distilling at 60° to 65° C./3 mm Hg. [Niedenzu, J. Am. Chem. Soc., 81, 5553 (1959)].

To a solution of N-methylanilinoborane dichloride (100 mg) in methylene chloride (5 ml), a solution of benzaldehyde (56 mg) and tri-n-butylamine (99 mg) in methylene chloride (2 ml) is added with ice cooling, and the resultant mixture is stirred at room temperature for 1 hour. The reaction mixture is mixed with ice pieces and shaken with methylene chloride. The methylene chloride layer is washed with aqueous sodium carbonate and a saturated brine in that order, and evaporated under reduced pressure to remove the solvent. The residue is chromatographed on a column of silica gel, and the product is recrystallized from chloroform-petroleum ether to give 2-methylaminobenzhydrol (85 mg) as crystals melting at 124° to 126° C. The yield is 75.0%.

EXAMPLES 8-12

Using the starting materials (I) and (II), the each reaction is effected as in Example 7, whereby the corresponding product (III) is obtained.

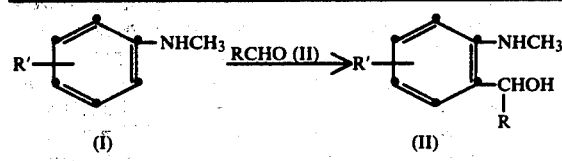

| Example No. | I R' | II R | Yield (%) | m.p. (°C.) | IR (CHCl₃, cm⁻¹) |
|---|---|---|---|---|---|
| 8 | H | m-NO₂—Ph | 83.3 | 125-126 | 3605, 3445 |
| 9 | H | p-CH₃O—Ph | 83.5 | 189-191* (d) | 3588, 3428 |
| 10 | H | PhCH=CH— | 49.6 | 154-156* | 1727, 1644, 1529, 1349* |
| 11 | H | 2-Furyl | 62.0 | 184-186* | 1730, 1645, 1528, 1349* |
| 12 | H | Pr | 38.3 | 131-133* | 3595, 3425 |

Note:
Pr (Propyl group).
*means that the measurement was effected on the O,N—di-p-nitrobenzoate.

EXAMPLE 13

To a solution of boron trichloride (4.5 g) in methylene chloride (3 ml), a solution of diphenylamine (6.5 g) in methylene chloride (12 ml) is added with cooling at −70° C., and the resultant mixture is stirred for 1 hour. The precipitated crystals are filtered at room temperature, washed with benzene, mixed with benzene (10 ml), and refluxed for 20 hours. After cooling, the reaction mixture is filtered to remove the insoluble material and evaporated under reduced pressure to remove the solvent. The residue is distilled under reduced pressure to give diphenylaminoborane dichloride (1.34 g) as an oil boiling at 117° to 120° C./0.9 mm Hg. M.P. 65°-69° C. [Gerrard, et al., J. Chem. Soc., 5168 (1960)].

Using diphenylaminoborane dichloride (200 mg), benzaldehyde (85 mg) and tri-n-butylamine (147 mg), the reaction is effected as in Example 7, whereby 2-phenylaminobenzhydrol (49 mg) is obtained. This substance is recrystallized from benzene-hexane to give crystals melting at 111° to 112° C. Anal. Calcd. for C₁₉H₁₇ON: C, 82.88; H, 6.62; N, 5.09. Found: C, 82.67; H, 6.28; N, 5.03.

IR, $\nu_{max}^{CHCl_3}$ 3597, 3405, 1594 cm⁻¹

NMR, δ(CDCl₃): 5.89 (1 H, s.), 6.62-7.47 (14H, m., Ar. H).

EXAMPLE 14

To a solution of p-ethoxycarbonyl-methylaniline (179 mg) in dry benzene (2 ml), a solution of boron trichloride (129 mg) in dry benzene (2 ml), is added with ice cooling. A solution of benzaldehyde (0.1 ml) and triethylamine (222 mg) in dry benzene (3 ml) is added to the mixture, which is stirred at room temperature for 3 hours. The reaction mixture is mixed with water and shaken with ether. The organic layer is washed with water, dried, and evaporated to remove the solvents. The residue is washed with petroleum ether to give 2-methylamino-5-ethoxycarbonylbenzhydrol (196 mg) as crystals melting at 132° to 135° C. The yield is 69%.

Anal. Calcd. for C₁₇H₁₉NO₃: C, 71.56; H, 6.71; N, 4.91. Found: C, 71.45; H, 6.87; N, 4.97.

IR, $\nu_{max}^{Nujol}$ 3417, 3357, 1666 cm⁻¹.

NMR, δ(CDCl₃): 1.3 (3H, t., J=7 Hz, OCH₂CH₃), 2.75 (3H, s., N—CH₃), 4.25 (2H, q., J=7 Hz, OCH₂—CH₃), 5.75 (1 H, s., —CH—OH), 6.4-7.9 (8H, m.).

What is claimed is:

1. In a process which comprises reacting an N-monosubstituted aniline with boron tribromide or boron trichloride to form the corresponding N-monosubstituted anilinoborane dihalogenide, the improvement wherein said N-monosubstituted anilino-borane dihalogenide is subsequently reacted with about 1.0 to about 1.5 mol equivalents, per equivalent of said N-monosubstituted aniline, of an aldehyde selected from the group consisting of paraldehyde and compounds of the formula RCHO wherein R represents a member selected from the group consisting of hydrogen, methyl, ethyl, propyl, butyl, pentyl, hexyl, amyl, stearlyl, vinyl, propenyl, butenyl, pentenyl, cyclopropyl, cyclobutyl, cyclopentyl, cyclohexyl, benzyl, phenethyl, phenylpropyl, phenylpentyl, phenylvinyl, phenylpropenyl, phenylbutenyl, phenyl, tolyl, xylyl, naphthyl, pyridyl, thienyl and furyl, said R being unsubstituted or substituted by chlorine, bromine, iodine, fluorine, methyl, ethyl, propyl, ispropyl, butyl, isobutyl, pentyl, methoxy, ethoxy, propoxy, butoxy, acetoxy, methoxycarbonyl, ethoxycarbonyl, propoxycarbonyl, butoxycarbonyl, trifluoromethyl, nitro or cyano, in the presence of at least about 1.0 mol equivalent, per equivalent of said N-monosubstituted aniline, of a base selected from the group consisting of t-butylisopropylamine, diisopropylamine, di-t-butylamine, dicyclohexylamine, t-butylcyclohexylamine, isopropylcyclohexylamine, t-butylaniline, isopropylaniline, cyclohexylaniline, diphenylamine, triethylamine, tripropylamine, triisopropylamine, tributylamine, triisobutylamine, dibutylethylamine, dipropylisopropylamine, diisopropylethylamine, diisobutylamine, butylethylpropylamine, dipropylbutylamine, methylpyrrolidine, ethyldicyclohexylamine, butyldicyclohexylamine, ethylpiperidine, propylmorpholine, dimethylaniline, diethylaniline, methylethylaniline, dimethylbenzylamine, diethylbenzylamine, methylethylbenzylamine, picoline, 2,6-luthidine, 2,4,6-collidine, pyridine, 2-isopropylpyridine and 2-t-butylpyridine at a temperature from about −30° C. to about 100° C. to regiospecifically introduce a 1-hydroxyalkyl or 1-hydroxysubstituted alkyl group into the ortho position of said N-monosubstituted aniline and thus produce an o-(N-monosubstituted amino) benzyl alcohol.

2. A process according to claim 1, wherein the benzene ring of said N-monosubstituted aniline is unsubstituted or monosubstituted.

3. In a process which comprises reacting an N-monosubstituted aniline with boron tribromide or boron trichloride to form the corresponding N-monosubstituted anilinoborane dihalogenide, the improvement wherein said reaction is carried out in the presence of about 1.0 to about 1.5 mol equivalents, per equivalent of said N-monosubstituted aniline, of an aldehyde selected from the group consisting of paraldehyde and compounds of the formula RCHO wherein R represents a member selected from the group consisting of hydrogen, methyl, ethyl, propyl, butyl, pentyl, hexyl, amyl, stearlyl, vinyl, propenyl, butenyl, pentenyl, cyclopropyl, cyclobutyl, cyclopentyl, cyclohexyl, benzyl, phenethyl, phenylpropyl, phenylpentyl, phenylvinyl, phenylpropenyl, phenylbutenyl, phenyl, tolyl, xylyl, naphthyl, pyridyl, thienyl and furyl, said R being unsubstituted or substituted by chlorine, bromine, iodine, fluorine, methyl, ethyl, propyl, isopropyl, butyl, isobutyl, pentyl, methoxy, ethoxy, propoxy, butoxy, acetoxy, methoxycarbonyl, ethoxycarbonyl, propoxycaarbonyl, butoxycarbonyl, trifluoromethyl, nitro or cyano, and in the presence of at least about 1.0 mol equivalent, per equivalent of said N-monosubstituted aniline, of a base selected from the group consisting of t-butylisopropylamine, diisopropylamine, di-t-butylamine, dicyclohexylamine, t-butylcyclohexylamine, isopropylcyclohexylamine, t-butylaniline, isopropylaniline, cyclohexylaniline, diphenylamine, triethylamine, tripropylamine, triisopropylamine, tributylamine, triisobutylamine, dibutylethylamine, dipropylisopropylamine, diisopropylethylamine, diisobutylamine, butylethylpropylamine, dipropylbutylamine, methylpyrrolidine, ethyldicyclohexylamine, butyldicyclohexylamine, ethylpiperidine, propylmorpholine, dimethylaniline, diethylaniline, methylethylaniline, dimethylbenzylamine, diethylbenzylamine, methylethylbenzylamine, picoline, 2,6-luthidine, 2,4,6-collidine, pyridine, 2-isopropylpyridine and 2-t-butylpyridine at a temperature from about −30° C. to about 100° C. to regiospecifically introduce a 1-hydroxyalkyl or 1-hydroxysubstituted alkyl group into the ortho position of said N-monosubstituted aniline and thus produce an o-(N-monosubstituted amino) benzyl alcohol.

4. A process according to claim 3, wherein the benzene ring of said N-monosubstituted aniline is unsubstituted or monosubstituted.

5. A process according to claim 1, wherein the each reaction is effected in an inert solvent.

6. A process according to claim 3, wherein the reaction is effected in an inert solvent.

7. A process according to claim 1, wherein boron trichloride is employed in the reaction.

8. A process according to claim 7, wherein the reaction with boron trichloride is effected in an inert solvent.

* * * * *